US007958201B2

(12) United States Patent
Lindsay

(10) Patent No.: US 7,958,201 B2
(45) Date of Patent: Jun. 7, 2011

(54) METHOD, SYSTEM AND APPARATUS FOR ENCOURAGING FREQUENT AND PURPOSEFUL ELECTRONIC COMMUNICATIONS FROM CAREGIVERS TO INDIVIDUALS WITH IMPAIRED MEMORY

(76) Inventor: Ted Lindsay, Ocala, FL (US)

( * ) Notice: Subject to any disclaimer, the term of this patent is extended or adjusted under 35 U.S.C. 154(b) by 19 days.

(21) Appl. No.: 12/583,107

(22) Filed: Aug. 13, 2009

(65) Prior Publication Data

US 2010/0191824 A1  Jul. 29, 2010

Related U.S. Application Data

(60) Provisional application No. 61/206,445, filed on Jan. 29, 2009.

(51) Int. Cl.
| G06F 15/16 | (2006.01) |
| G06F 19/00 | (2006.01) |
| G06F 15/173 | (2006.01) |
| G06Q 10/00 | (2006.01) |
| G06Q 50/00 | (2006.01) |

(52) U.S. Cl. ............... 709/217; 705/2; 705/3; 715/729; 379/106.02; 379/52; 704/271; 706/924; 340/539.12

(58) Field of Classification Search .......... 709/217–228; 715/729; 379/106.02, 52; 704/271; 706/924; 340/539.12; 705/2, 3
See application file for complete search history.

(56) References Cited

U.S. PATENT DOCUMENTS

| 6,961,458 | B2 * | 11/2005 | Dutta et al. | 382/154 |
| 7,457,656 | B2 * | 11/2008 | Judd et al. | 600/407 |
| 7,526,485 | B2 * | 4/2009 | Hagan et al. | 705/3 |
| 7,542,913 | B1 * | 6/2009 | Meek et al. | 705/4 |
| 7,584,108 | B2 * | 9/2009 | Brown | 705/2 |
| 7,590,549 | B2 * | 9/2009 | Brown | 705/2 |
| 7,606,720 | B1 * | 10/2009 | Kerpelman et al. | 705/2 |
| 7,636,667 | B2 * | 12/2009 | Brown | 705/2 |
| 7,644,077 | B2 * | 1/2010 | Picker et al. | 707/783 |
| 7,647,320 | B2 * | 1/2010 | Mok et al. | 707/770 |
| 7,676,368 | B2 * | 3/2010 | Shizuka et al. | 704/260 |
| 7,689,544 | B2 * | 3/2010 | Koenig | 707/741 |
| 7,693,728 | B2 * | 4/2010 | Underwood et al. | 705/2 |
| 7,711,578 | B2 * | 5/2010 | Williams et al. | 705/2 |
| 7,742,930 | B1 * | 6/2010 | Calhoun et al. | 705/2 |
| 7,774,134 | B1 * | 8/2010 | Bleser et al. | 701/207 |
| 7,774,215 | B2 * | 8/2010 | Rosow et al. | 705/2 |
| 7,774,273 | B2 * | 8/2010 | Neal et al. | 705/39 |
| 2002/0002474 | A1 * | 1/2002 | Michelson et al. | 705/3 |
| 2002/0019753 | A1 * | 2/2002 | Boden | 705/3 |
| 2008/0154099 | A1 * | 6/2008 | Aspel et al. | 600/301 |
| 2009/0070148 | A1 * | 3/2009 | Skocic | 705/3 |
| 2009/0157807 | A1 * | 6/2009 | Brown et al. | 709/203 |
| 2009/0212956 | A1 * | 8/2009 | Schuman et al. | 340/573.1 |
| 2010/0049547 | A1 * | 2/2010 | Mirza et al. | 705/3 |
| 2010/0063822 | A1 * | 3/2010 | O'Brien et al. | 704/271 |

\* cited by examiner

*Primary Examiner* — Haresh N Patel
(74) *Attorney, Agent, or Firm* — Massinger Law Offices

(57) ABSTRACT

A computer implemented system and method for encouraging frequent and purposeful electronic communications from caregivers to individuals with impaired memory to, inter alia, alleviate feelings of isolation and improve memory. The system includes a Web-based application through which caregivers send text, image, voice and other forms of data for receipt by the sufferer on a PDA having a simple user interface. The Web application records the dates and nature (i.e., text, audio, photograph, video) of communications sent by each caregiver, processes the data in order to display it in a variety of meaningful ways to all caregivers, thus creating a peer-pressure environment to encourage more frequent communication. The Web application can also be programmed to send electronic reminders to all caregivers who opt-in to the service requesting that they send a communication to the sufferer, and more particularly to individual caregivers whose frequency of communication has been inadequate relative to a group of caregivers or to predefined expectations.

6 Claims, 13 Drawing Sheets

SMS Message Filter 12

PDA Client Application Updates Sent to Web Application

Conceptual Web Site - Secondary Caregiver

Communication Mechanism using Web Based UI

Reminder Mechanism using SMS

METHOD, SYSTEM AND APPARATUS FOR ENCOURAGING FREQUENT AND PURPOSEFUL ELECTRONIC COMMUNICATIONS FROM CAREGIVERS TO INDIVIDUALS WITH IMPAIRED MEMORY

RELATED APPLICATION

This application claims the benefit of U.S. Provisional Application No. 61/206,445, filed Jan. 29, 2009 and entitled, Method, System, And Apparatus For Supporting Individuals With Impaired Memory.

FIELD OF THE INVENTION

The present invention relates to a method, system, and apparatus for encouraging frequent and purposeful electronic communications from caregivers to individuals with impaired memory.

BACKGROUND

People with memory impairment ("sufferers") lack an awareness of the actions, events, and experiences of their everyday lives. This lack of continuity in their lives and can lead to confusion, embarrassment, isolation, depression, a loss of independence and sense of self, and impaired decision-making. One common cause of memory impairment is Alzheimer's disease (AD). One of the earliest symptoms of AD and Mild Cognitive Impairment (a condition that often precedes AD) is loss of the ability to recall memories of recent experiences.

Supporting a sufferer through frequent personal contact and the sharing of information relating to people, places and things, whether past, present or future, has many benefits such as a decrease or elimination of the sufferer's sense of isolation, an increase in the sufferer's confidence, independence, and overall quality of life, and possibly an increase in the sufferer's ability to recall memories. All these benefits not only benefit the sufferer, but the sufferer's primary caretaker such as a spouse or adult child of the sufferer, or a hired professional caregiver. Familial primary caretakers more often than not feel overwhelmed with the responsibility of caring for the sufferer and a sense of heartbreak and helplessness as they watch a person they love slowly lose their faculties. Both familial and professional primary caretakers desperately seek assistance from other people close to the sufferer such as family and friends. Unfortunately, some such individuals are often geographically distant from the caretaker, making frequent visits impossible, and all too often leads to an "out-of-sight, out-of-mind" situation. What's worse, some individuals slowly shy away from contact with the sufferer because communication with someone suffering from memory loss can be extremely difficult and uncomfortable. As a result, the primary caretaker too feels a sense of isolation and despair, sometimes being the only person providing round-the-clock care. Certainly there is a need for an automated means of encouraging the transmission of more frequent and meaningful communications to a sufferer by those who are unable to or uncomfortable with making personal visits.

There have been proposed various methods and apparatus for monitoring and/or assisting individuals with special needs such as those suffering with memory impairment. The following patents are illustrative and incorporated herein by reference: U.S. Pat. No. 5,169,342 entitled, Method of Communication with a Language Deficient Patient; U.S. Pat. No. 5,890,905 entitled, Educational and Life skills Organizer/Memory Aid; U.S. Pat. No. 6,540,674 entitled, System and Method for Supervising People with Mental Disorders; U.S. Pat. No. 6,611,206 entitled, Automatic System for Monitoring independent Person Requiring Occasional Assistance; U.S. Pat. No. 6,828,918 entitled Personalized Accessibility Identification Receiver/Transmitter and Method for Providing Assistance; U.S. Pat. No. 6,950,026 entitled, Method for Complementing Personal Lost Memory Information with Communication, and Communication System, and Information Recording Medium Thereof; U.S. Pat. No. 7,058,208 entitled, Method and Apparatus of Managing Information About a Person; U.S. Pat. No. 7,095,328 entitled, System and Method for Non-Intrusive Monitoring of At Risk Individuals; U.S. Pat. No. 7,409,045 entitled, Lifestyle Multimedia Security System; and U.S. Patent Application 20010040986 entitled, Memory Aid.

The following patents relate to devices used in monitoring the condition or activity level of an individual: U.S. Pat. No. 6,646,873 entitled, Personal Digital Assistant for Connecting with a Communications Module; U.S. Pat. No. 6,774,795 entitled, Electronic Assistant Incorporated in Personal Objects; U.S. Pat. No. 6,812,824 entitled, Method and Apparatus Combining a Tracking System and Wireless Communication System; U.S. Pat. No. 6,856,898 entitled, PDA systems, Functional Data, and Methods to Bias Map matching; U.S. Pat. No. 6,868,074 entitled, Mobile Data Device and Method of Locating Mobile Data Device; U.S. Pat. No. 6,904,363 entitled, System for Local Monitoring; U.S. Pat. No. 7,317,927 entitled, Method and System to Monitor Persons Utilizing Wireless Media; and PCT Publication WO 97/25697 entitled, Method and Apparatus for Monitoring Persons in a Dwelling.

The following patents relate to cognitive testing or learning: U.S. Pat. No. 5,260,869 entitled, Communication and Feedback System for Promoting Development of Physically Disadvantaged Persons; U.S. Pat. No. 6,159,014 entitled, Method and Apparatus for Training of Cognitive and Memory Systems in Humans; U.S. Pat. No. 6,270,456 entitled, Computerized Medical Diagnostic System Utilizing List-Based Processing; U.S. Pat. No. 6,280,198 entitled, Remote Computer Implemented Methods For Cognitive Testing; U.S. Pat. No. 6,513,046 entitled, Storing and Recalling Information to Augment Human Memory; and U.S. Pat. No. 6,524,239 entitled, Apparatus for Non-intrusively Measuring Health Parameters of a Subject and Method of Use Thereof.

None of the above patents, alone or in combination, teach a system, method or apparatus for encouraging caregivers to transmit electronic communications to an individual with impaired memory.

All patents, patent applications, provisional applications, and publications referred to or cited herein, or from which a claim for benefit of priority has been made, are incorporated herein by reference in their entirety to the extent they are not inconsistent with the explicit teachings of this specification.

SUMMARY OF THE INVENTION

The present invention solves the need in the art by providing a method, system, and apparatus for supporting individuals with impaired memory as well as their primary caregivers. Features of the invention can be implemented in numerous ways, including as a system and a method. Portions of the invention are embodied on computing devices, including a personal digital assistant ("PDA") which is carried by a sufferer, and on a computer site hosting a Web-based application.

The invention preferably utilizes a communications infrastructure, for example the Internet, wherein remote communication is possible. Several embodiments of the invention are discussed below.

More specifically, the subject invention as a system is comprised very generally of four primary components interconnected via a communication infrastructure: 1) a Web application running on a Web server, 2) a PDA Client Application running on a PDA device, 3) a primary caregiver computing device operated by a primary caregiver, and 4) at least one secondary caregiver computing device operated by at least one secondary caregiver. The PDA and other computing devices are all network accessible.

The Web application serves as a central hub for storing information about subscribing sufferers, managing information transmitted by subscribing sufferers and their primary and secondary caregivers to the Web application for processing, and facilitating and encouraging communication between each individual subscribing sufferer and his or her primary and secondary caregivers through the communications infrastructure. The communications infrastructure comprises one or more of Internet, Intranet, telephone interface, cellular interface, satellite, WAN, LAN, or the like.

The first primary component, the Web application, is comprised of three subcomponents: a) a User Interface (UI) comprised of Web pages accessible over the Internet and used by both primary and secondary caregivers; 2) a Main .Net Web application including all business logic of the system for facilitating communication between all other components; and 3) a Main database preferably but not essentially comprised of an SQL database that stores all information related to accounts, caregivers, sufferers, application configuration and PDA devices.

The second primary component, the PDA Client Application runs on a PDA and is comprised of two subcomponents: a) a .Net client application for all subscriber side business logic as well as a user interface; and b) a Simple Message System (SMS) Message Interceptor—registered with, for example, Windows Mobile system for intercepting all incoming SMS messages, filtering the ones coming from the Web application and passing them on to the .Net client application.

The above inter-related components provide a means for carrying out a computer implemented method of encouraging friends, family and other such individuals (caregivers) of an individual suffering from memory impairment (sufferer) to communicate more frequently and more purposefully with the sufferer to reduce feelings of isolation, loneliness, low self-worth, confusion, agitation, embarrassment and deteriorating quality of life associated with their impairment. This is accomplished, in part, by providing a Web-based service to which the sufferer subscribes and through which caregivers send text, image, voice and other forms of data for receipt by the sufferer on a PDA having a simple user interface. The Web application tracks and records the dates and type (i.e., text, photograph, video) of communications sent by each caregiver and displays them on a webpage for all other caregivers to see, thus creating a peer-pressure environment to encourage more frequent communication. The Web application can also be programmed to send electronic reminders to all caregivers who opt-in to the service requesting that they send a communication to the sufferer, and more particularly to individual caregivers whose frequency of communication has been inadequate relative to a group of caregivers or to predefined expectations.

There has thus been outlined, rather broadly, the more important components of the system of the subject invention in order that the detailed description thereof that follows may be better understood, and in order that the present contribution to the art may be better appreciated. There are, of course, additional features of the invention that will be described hereinafter and which will form the subject matter of the claims appended hereto. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

By virtue of the above described system the various methods of the subject invention may be carried out to accomplish multiple objectives as set out below.

It is a primary objective of the subject invention to provide a computer implemented method of encouraging caregivers to engage an individual suffering from impaired memory on a frequent basis and in a meaningful way to promote self-sufficiency and cognition, all under the direction and supervision of a primary caretaker such as a close family member, friend or professional caretaker. This is accomplished, in part, by providing a hand-held computing device such as a PDA having a simple user interface which is carried by the sufferer and through which the sufferer receives, inter alia, memory invoking messages in the form of text, images, voice and video sent by his or her caretakers through a Web based application. The PDA is connected via a communications infrastructure to the Web application which is accessible by both a primary caretaker and secondary caretakers who can review the frequency and nature of each other's communications with the sufferer thereby creating a peer pressure environment.

By increasing the frequency and quality of communications from caregivers to the sufferer, another object of the subject method, system and apparatus is achievable, namely providing "supplemental memory" to the sufferer and as the memory loss increases for providing "surrogate memory."

It is another object of the subject invention to store communications received from caregivers thereby creating an archive of memories which may be easily accessed by the sufferer on their PDA. These message contacts are critical to the sufferer's quality of life. The outside contact provides engagement in life thereby extending and exercising the sufferers' cognizance. The unique aspect of this message system is that it is "care" related. All caregivers are encouraged to make contact which is "scored" on the website through which they enter.

It is another object of the subject invention to provide a method, system and apparatus for supporting memory impaired which conforms to related science and opinion relative to memory loss and its treatment.

These together with other objects of the invention, along with the various features of novelty which characterize the invention, are pointed out with particularity in the claims annexed to and forming a part of this disclosure. For a better understanding of the invention, its advantages and the specific objects attained by its uses, reference should be had to the accompanying drawings and descriptive matter in which there is illustrated a preferred embodiment of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

Figure 1:
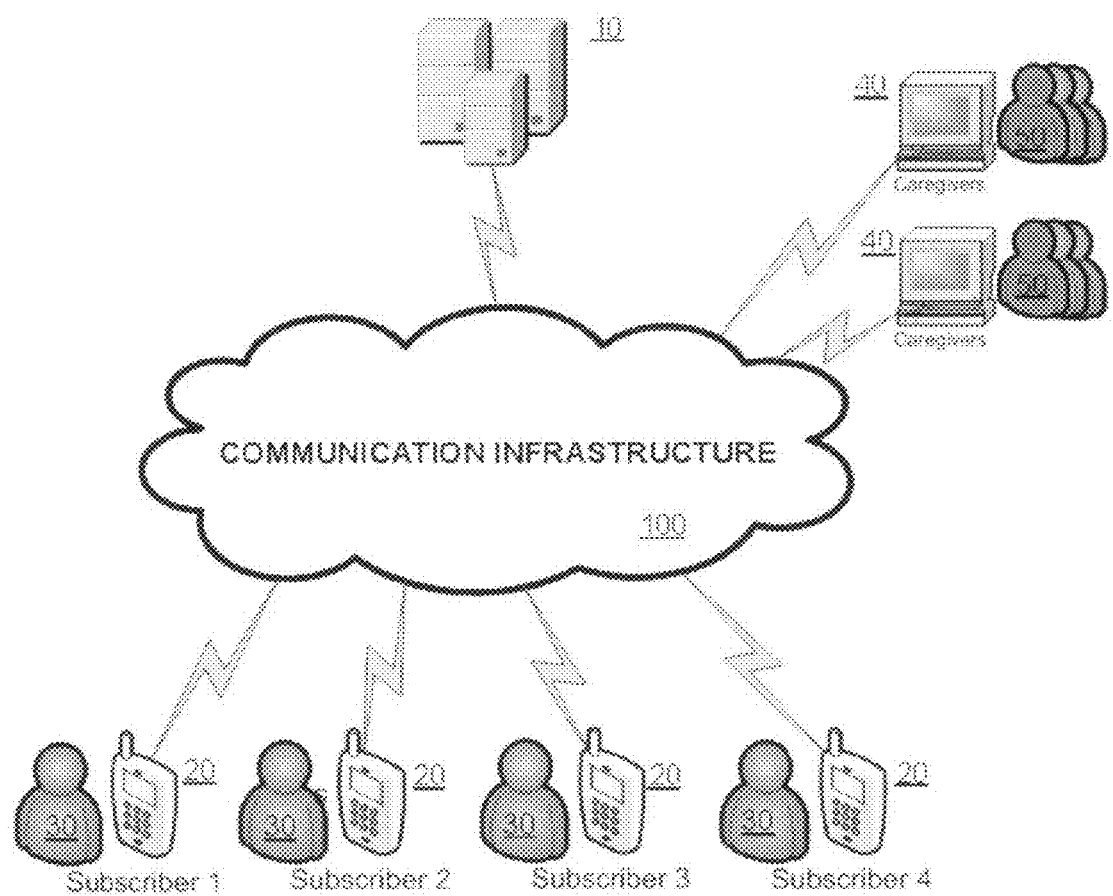
FIG. 1 illustrates an embodiment of the subject system for supporting individuals with impaired memory, the system including a Web-based server, PDA's carried by subscribing sufferers and computing devices employed by their caregivers, all interconnected via a communications infrastructure.

It should be understood that in certain situations for reasons of computational efficiency or ease of maintenance, the ordering of the blocks of the illustrated flow charts could be rearranged or moved inside or outside of the illustrated loops by one skilled in the art. While the present invention will be described with reference to the details of the embodiments of the invention shown in the drawing, these details are not intended to limit the scope of the invention.

DETAILED DESCRIPTION OF PREFERRED EMBODIMENTS

Reference will now be made in detail to the embodiments consistent with the invention, examples of which are illustrated in the accompanying drawings. Wherever possible, the same reference numerals used throughout the drawings refer to the same or like parts.

Figure 2:
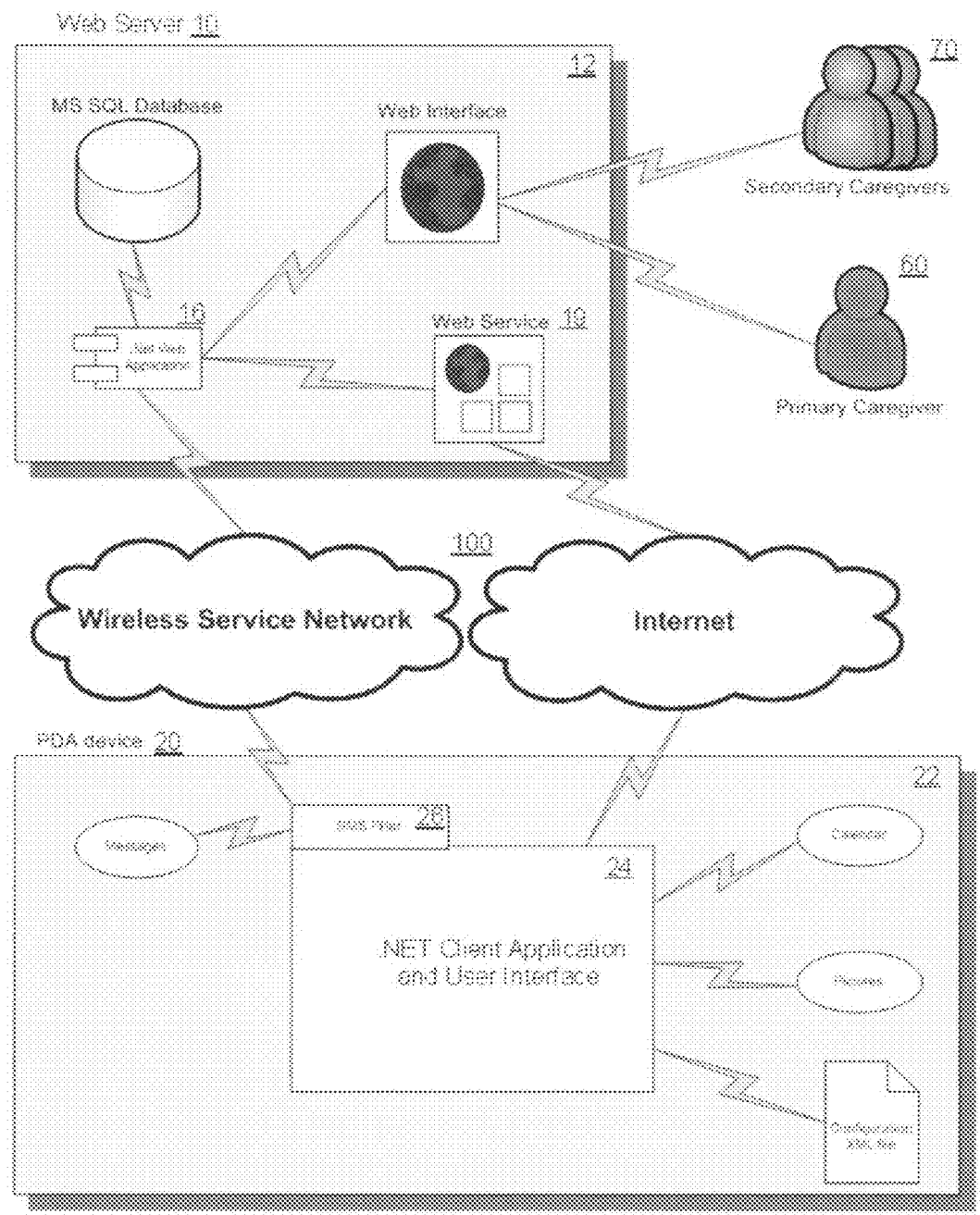
FIG. 2 illustrates the application architecture of the Web server used by the sufferer's primary and secondary caregivers as well as that of the PDA device of the subject system and their interconnection via a communications infrastructure.

Turning now specifically to FIG. 1, an embodiment of the subject invention as a system is comprised very generally of a Web-based server 10, at least one computing device, preferably a Personal Digital Assistant ("PDA") 20 carried by at least one subscribing sufferer 30 and at least one caregiver computing device 40 employed by at least one caregiver 50, all interconnected via a communications infrastructure 100. Subscribing sufferer 30 refers to an individual suffering from memory and/or other cognitive impairment (sometimes referred to herein as "patient") and who has opened an account, directly or indirectly, with a provider of the subject system ("service provider"). Caregiver 50 refers to one or more of a primary caregiver 60 and a secondary caregiver 70 (FIG. 2). Communications infrastructure 100 comprises one or more of Internet, Intranet, telephone interface, cellular interface, satellite, WAN, LAN, or the like. PDA 20 and other computing devices 40 are all network accessible.

Reference now being made to FIG. 2, the application architecture associated with Web server 10 and PDA 20 is illustrated. In a preferred embodiment Web server 10 hosts a Web application 12 which is accessible by primary caregiver 60 and secondary caregivers 70 when an account is opened by or for the benefit of a sufferer 30. Web application 12 serves as a central hub for storing information about subscribing sufferers 20, managing information transmitted between subscribing sufferers 20 and their caregivers 50 on the one hand, and the Web application on the other, via the communications infrastructure 100.

The Web application, is comprised of three subcomponents: 1) a User Interface 14 (UI) available to both primary caregivers 60 and secondary caregivers 70 through Web pages accessed by a caretaker computing device having a Web browser; 2) a Main .Net Web application 16 including all business logic of the system for facilitating communication between all other components; and 3) a Main database 18 preferably but not essentially comprised of an SQL database that stores all information related to accounts, caregivers, sufferers, application configuration and at least one PDA device 20. The Web application is preferably a C# based ASP .Net web application with MS SQL 2005/2008 back-end database which is scalable to support millions of subscribers. Regardless of the type of UI used by the caregiver, all UIs relay caregiver's communication to the sufferer through the Web application 12 which serves as the hub for further distribution of communication (text messages, pictures, videos) to the intended sufferer.

With continued reference to FIG. 2, a PDA Client Application 22 runs on a PDA 20 and is comprised of two subcomponents: a) a .Net Client Application and User Interface 24 for all subscriber side business logic as well as a user interface;

and b) a Simple Message System (SMS) Message Interceptor 26—registered with, for example, Windows Mobile system for intercepting all incoming SMS messages, filtering the ones coming from the Web application and passing them on to the .Net client application. An example of a suitable PDA device 20 is a Windows Mobile Professional (6.1 or later) compatible device. The PDA Client Application 22 may be a C# application with XML configuration file used for caching purposes. This solution also provides rapid development of the subscriber side application, as well as provides the flexibility in choosing actual existing PDA devices and wireless network service providers.

Figure 3:
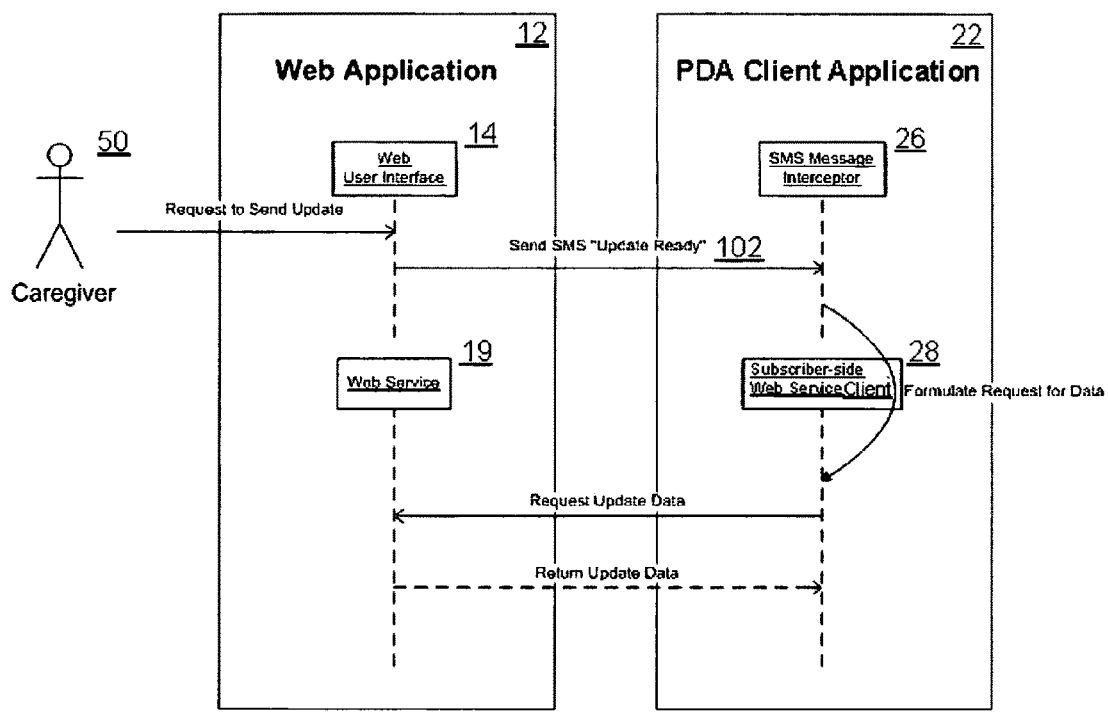
FIG. 3 is a diagrammatic illustration of the manner in which Web Application updates are sent to the PDA Application.
Figure 4:
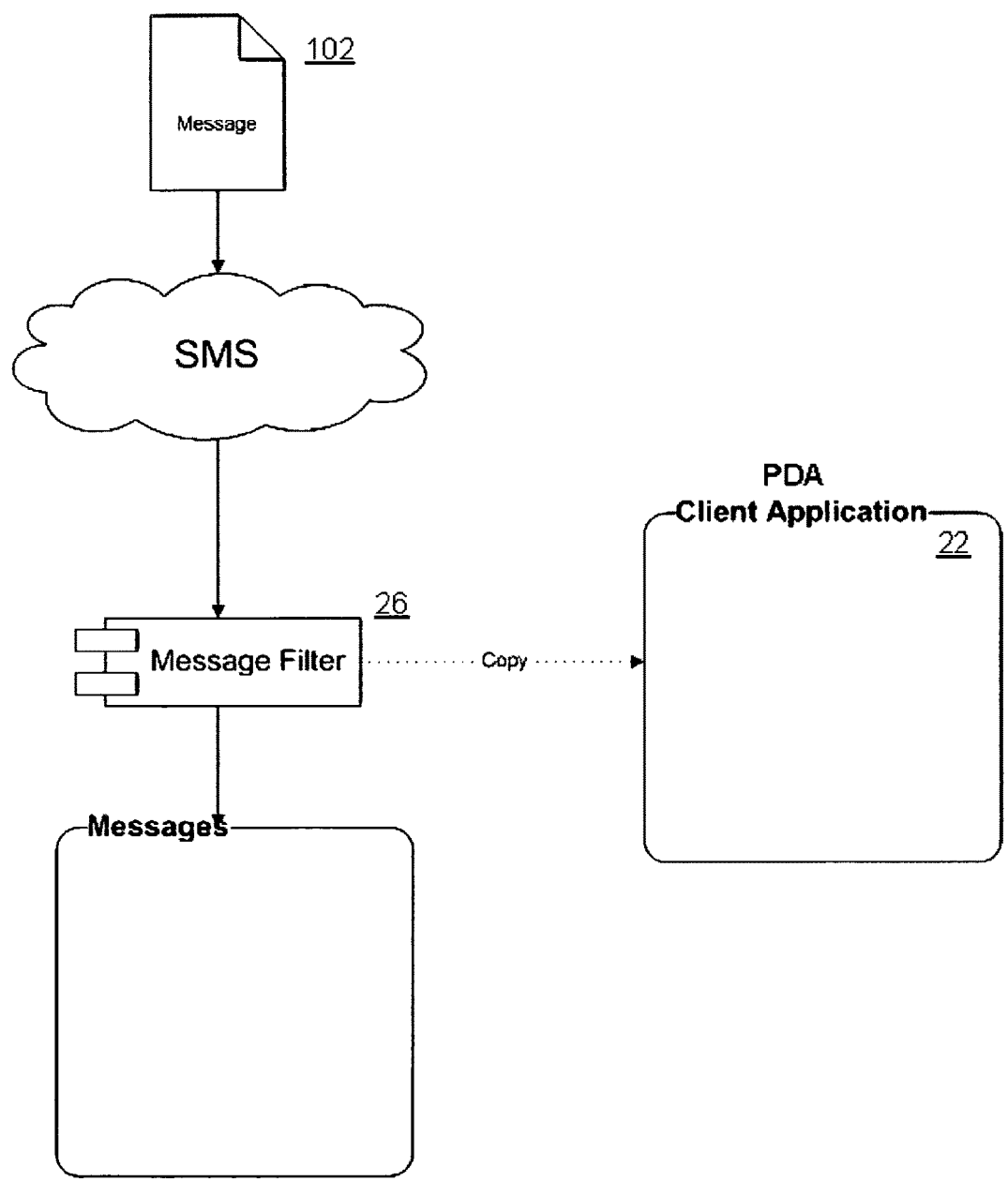
FIG. 4 is a diagrammatic illustration of the PDA Application's use of an SMS Message Interceptor component to receive "Update ready" message.

Communication between Web Application 12 and PDA Client Application 22 is executed in two modes: 1) where Web Application 12 updates are sent via a Web Application-side Web Service 19 to PDA Client Application 22, and 2) where PDA Client Application 22 updates are sent via a Subscriber-side Web Service 28 to Web Application 12. In the first instance, all update actions initiated by the caregiver 50 using the User Interface 14 of Web Application 12 are executed as shown in FIG. 3. The PDA Client Application 22 uses the SMS Message Interceptor 26 component to receive "Update ready" message 102 in a manner well known in the art and as illustrated in greater detail in FIG. 4.

Figure 5:
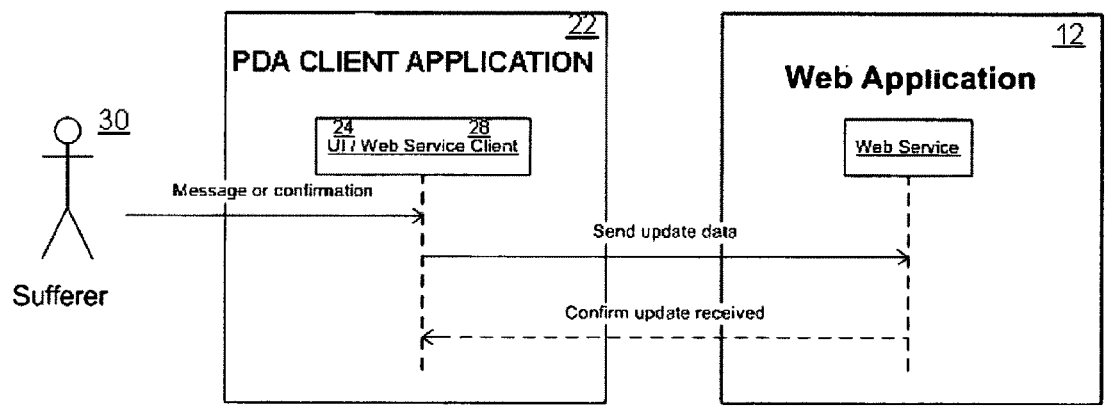
FIG. 5 is a diagrammatic illustration of the manner in which the PDA Application updates are sent to the Web Application.

In the second instance, all update actions initiated by sufferer 30 using Client Application and User Interface 24 are executed as shown in FIG. 5. Here again, Web Application-side Web Service 19 and Subscriber-side Web Service 28 serve as gateways for corresponding Web Application 12 and PDA Client Application 22.

It will be readily appreciated that the principles of the invention may apply to other computing devices, such as mainframes, minicomputers, network servers, supercomputers, personal computers, or workstations, as well as other electronics applications. Therefore, while the discussion herein focuses on a particular computing arrangement, it should be understood that the invention is not limited to the particular hardware designs, software designs, communications protocols, performance parameters, or application-specific functions disclosed herein. An apparatus for making, using or selling the invention may be one or more processing systems including, but not limited to, a central processing unit (CPU), memory, storage devices, communication links and devices, servers, I/O devices, or any sub-components of one or more processing systems, including software, firmware, hardware or any combination or subset thereof, which embody the invention as set forth in the claims. One skilled in the art of computer science will easily be able to combine the methods as described with appropriate general purpose or special purpose computer hardware/software to create a computer system or computer sub-system embodying the method of the invention.

The subject system may also be adapted for direct audio or audiovisual communication between caregivers 50 and sufferers 30 in a variety of conventional ways. As a first example, in its simplest form, a conventional phone may be used to send voice data to a sufferer's PDA device 20 which includes phone service. Similarly, a cellular phone may be used for direct communication with sufferer 30.

A variation of this is Internet telephony for the routing of voice conversations over the Internet or through any other IP-based network (e.g., Voice over Internet Protocol, also called VoIP, IP Telephony, Internet telephony, Broadband telephony, Broadband Phone and Voice over Broadband). Internet telephony may be advantageous for long distance calls to save toll charges, provided there is an Internet connection (wired or wireless) thus encouraging calls by caregivers 50.

Internet telephony may be incorporated into the caregiver's computer 40 so that an external communication device (e.g. telephone) is not necessary. Many computers incorporate microphones and/or built-in cameras making them audio/video messaging ready. The microphone would receive audio from the caregiver. The audio signal would then be transmitted to the sufferer via Internet telephony who would listen to the audio using speakers, earphones, or the like associated with the PDA 20.

As an example, Skype® (SKYPE LIMITED CORPORATION IRELAND) peer-to-peer Internet telephony (which offers free voice and video conferencing) relies on a software client on the computer in order to place a call over the network anywhere in the world. SkypeOut™ allows Skype users to call traditional telephone numbers, rather than other computer users with Skype communication software. SkypeIn™ allows Skype users to receive calls on their computers dialed by regular phone subscribers to a local Skype phone number. Skype supports group text chat with an interface similar to IRC. The Skype Wi-Fi Phone is a wireless mobile phone that allows users to make free Internet calls to anyone who has Skype, anytime there is a Wi-Fi wireless Internet connection.

Communications that include video may be implemented with known videoconferencing systems and the like. A videoconference (also known as a videoteleconference) is a set of interactive telecommunication technologies which allow two or more locations to interact via video and audio transmissions. The core technology used in a videoteleconference (VTC) system is digital compression of audio and video streams in real time. Skype 2.0 (and above), for example, supports videoconferencing. The components used with a VTC system include, for example, Video input (e.g., video camera or webcam), Video output (e.g., computer monitor, television or projector), Audio input (e.g., microphones), Audio output (e.g., loudspeakers associated with the display device or telephone), and Data transfer (e.g., analog or digital telephone network, LAN or Internet).

A videoconference system may be provided or may be incorporated into the caregiver's computer 40 having a built-in camera and microphone. The camera would capture images/video and the microphone would receive audio. The audio and video would be transmitted to the sufferer 30 who could view the video on the PDA 20 and listen to the audio using built-in speakers or the like.

For sending private messages between a caregiver and a sufferer, in one embodiment, the invention utilizes the transmission of an electronic message over a computer network using software that immediately displays the message in a window on the PDA screen of sufferer 30. Instant messaging or IM is a form of such real-time communication between two or more people based on typed text. The text is conveyed via computers connected over a network such as the Internet. Popular instant messaging services on the public Internet include .NET Messenger Service (MSN Messenger and Windows Live Messenger), AOL Instant Messenger, Excite/Pal, Gadu-Gadu, Google Talk, iChat, ICQ, Jabber, Qnext, QQ, Meetro, Skype, Trillian, Yahoo! Messenger and Rediff Bol Instant Messenger. One can also connect to an instant messaging service with a multiprotocol instant messaging application, which allows one instant messenger (IM) client to connect to multiple IM networks. Caregivers 50 can send private messages directly to the sufferer's PDA 20 in real-time using an instant messaging service.

For sending private messages between a caregiver 50 and a sufferer 30, in another embodiment, the invention utilizes an online chat medium, such as Internet Relay Chat (IRC). In still another embodiment, the private messages can be sent using a virtual whiteboard. Whiteboarding is a term used to describe the placement of shared files on an on-screen "shared notebook" or "whiteboard". Videoconferencing software such as TalkAndWrite, Groupboard, Windows Live Messenger, and BitWise IM include tools that let the user mark up the electronic whiteboard much as one would with a traditional wall-mounted board.

The extent to which the above described means of direct communication may be utilized depends on the level of technical acumen of the sufferer 30 as well as the degree of their cognitive impairment.

Figure 6:
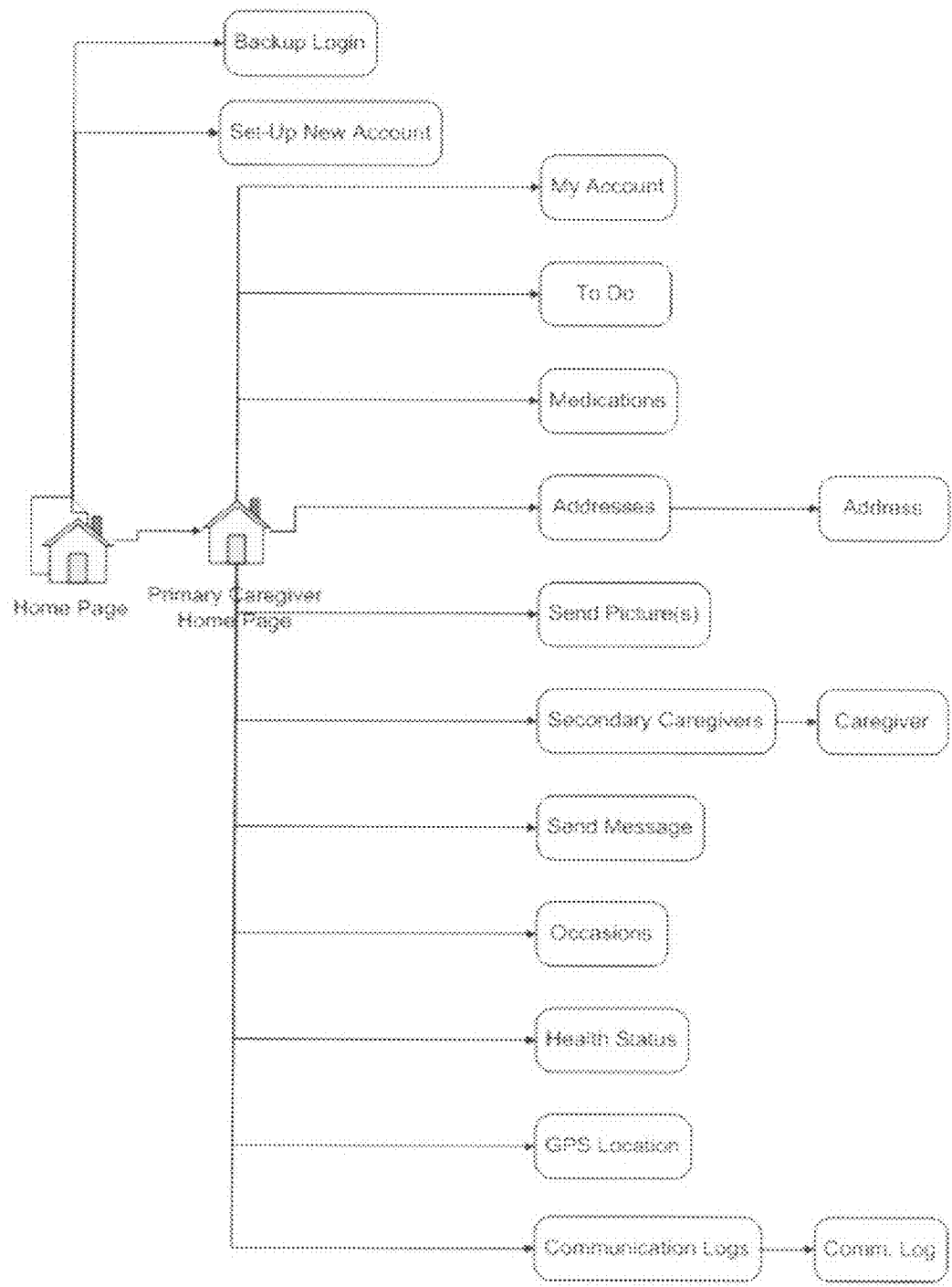
FIG. 6 is a diagrammatic illustration of an example home page for primary caregivers using the subject system.
Figure 7:
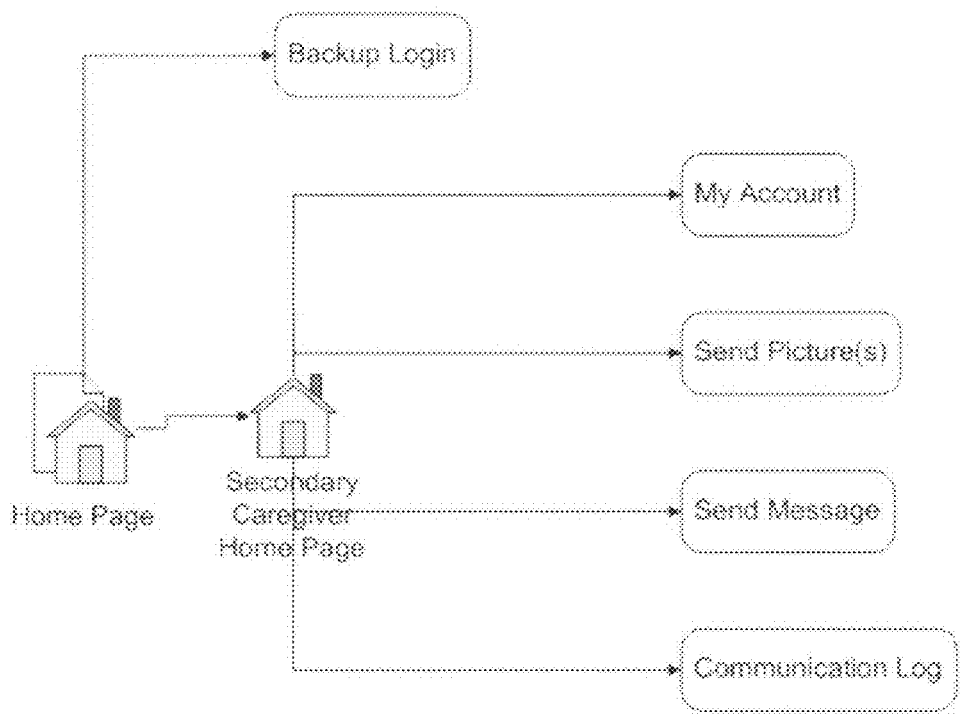
FIG. 7 is a diagrammatic illustration of an example home page for generic caregivers (both primary and secondary caregivers) using the subject system.

Referring now to FIGS. 6 and 7, with the above described system architecture in place, the following actions are carried out to set up an account for a sufferer, and to gain access to system by primary and secondary caregivers.

Account Formation and System Access

First, a prospective subscriber, typically a primary caregiver, accesses Web Application 12 (also "Web Site") via a Web browser on computer 40 to sign up for a new account. Essential information required for the account is entered by the subscriber and the account is created. A 'Primary Caregiver' account is created automatically for the person opening the new account and associated with the subscription account. The primary caregiver enters essential information required for the caregiver account (including mandatory login username and password). A unique email address must be provided for the caregiver. If the same email address is found in the database associated with any other caregiver account a different email address will be requested. No subscription is selected or payment performed at this point.

The primary caregiver for the account navigates to the subscription options and selects the 'add new sufferer' option. Subscription options are presented to the primary caregiver who then selects one subscription option and enters payment information. Web Application 12 verifies the payment, creates a new sufferer entity and associates it with the new account. The primary caregiver then enters the sufferer personal and contact information. Note that the primary caregiver can repeat this action and add additional subscriptions for additional sufferers.

The primary caregiver associated with the new account navigates to the 'add new caregiver' option and then enters the secondary caregiver's information and selects one or more sufferers associated with the new account to be associated with the new secondary caregiver. A unique email address must be provided for each secondary caregiver. If the same email address is found in the database associated with any other caregiver account, primary or secondary, a different email address will be requested. An email message is sent to the email address provided for the secondary caregiver with login information. Note that the primary caregiver can repeat this action and add additional secondary caregivers.

If not already selected, the primary caregiver selects one of the sufferers associated with the account and then navigates to the 'sufferer management' web page. The primary caregiver can change existing sufferer information (including health status, emergency contacts, etc.) or delete the sufferer from the account. After making changes the primary caregiver must confirm changes before they are applied to the database.

If not already selected, the primary caregiver selects one of the secondary caregivers associated with the account and then navigates to the 'caregiver management' web page. Here, the primary caregiver can change existing caregiver information, disassociate a caregiver from a sufferer, or delete the caregiver from the account. After making changes the primary caregiver must confirm changes before they are applied to the database.

If not already selected, the primary caregiver selects one of the sufferers associated with the account and then navigates to the 'sufferer contacts' web page. The primary caregiver uses the provided user interface to add new contacts (names, addresses, phones, pictures), and/or change or delete existing ones. On the 'sufferer contacts' page, the primary caregiver is presented with an option to send the update to the sufferer's PDA. The primary caregiver can choose this option to send updates at any time. It is not necessary that the primary caregiver send the update immediately after any change is made, as he/she may plan to review the changes and submit them at a later time. No changes are sent to the sufferer's PDA until the primary caregiver actually selects and confirms the 'send update' option.

Referring now to FIG. 7, the following actions are carried out by all secondary caregivers to gain access to and utilization of the system. For simplicity's sake, secondary caregivers shall be referred to as "caregiver(s)" which term shall specifically not include primary caregivers unless otherwise noted.

Each caregiver uses his/her login credentials to login to the account created by the primary caregiver. If login credentials are correct, the caregiver is authenticated. If login is unsuccessful, caregiver is forwarded to a new page where he/she can choose one of the following options:

Re-try the login
Remind me of my username
Reset my password
Not registered. Register for new account If the caregiver is a primary caregiver, login is successful and no sufferer subscription exists, the primary caregiver is presented with an option to 'create new sufferer'. If at least one sufferer subscription exists, the caregiver is presented with the 'primary caregiver main menu'. If the caregiver is a secondary caregiver, a 'secondary caregiver main menu' is presented.

Each unauthenticated caregiver navigates to 'remind me of my username' option, enters his/her email address associated with his/her caregiver account and confirms the request. If his/her email address is found in database, an email, containing associated caregiver's username is sent to the email address.

Each unauthenticated caregiver may navigate to the 'reset my password' option, enter his/her username and email address associated with his/her caregiver account and confirm the request. If the provided username and email address provided match with the information in the database associated with Web application 12, the caregiver's password is reset to a random value and email is sent to the email address associated with the account. The email contains the new random password and a link to a login page. The caregiver is instructed to change his/her password immediately after successful login.

Transmitting and Logging Communications to the Sufferer

Figure 8:
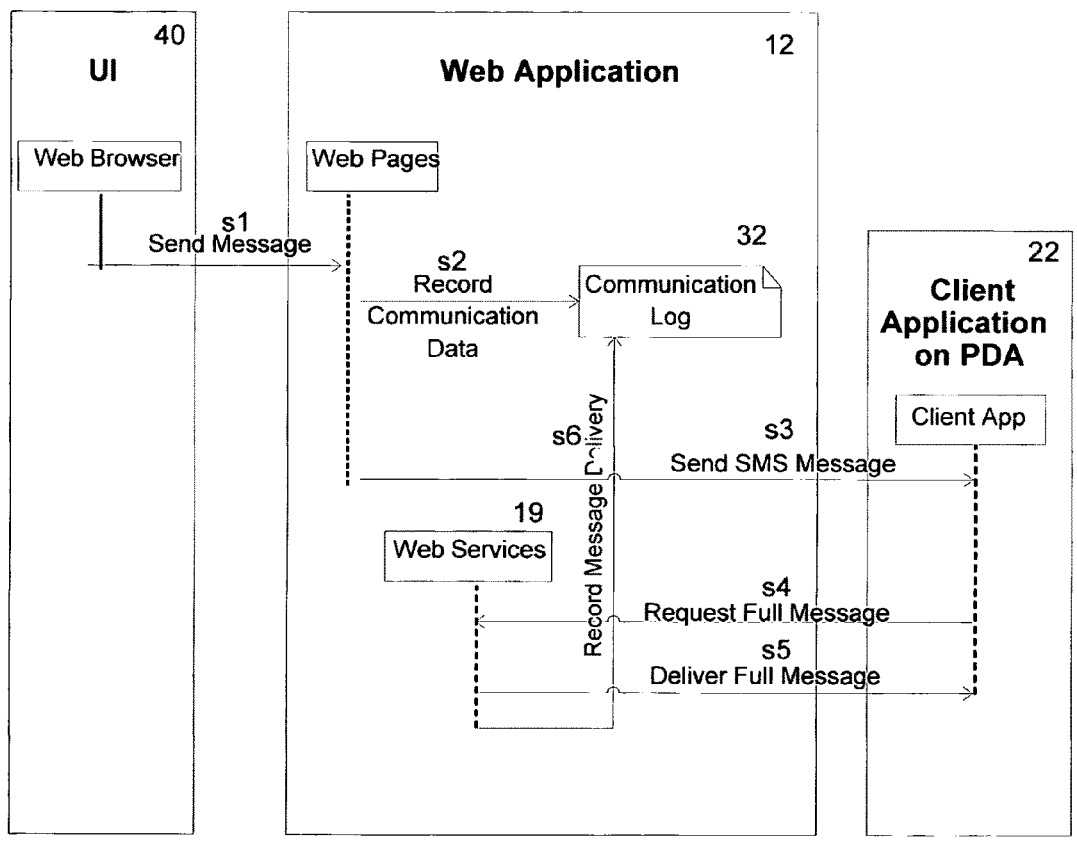
FIG. 8 is a diagrammatic illustration of the method by which a communication is transmitted by a caregiver to a sufferer using a Web based user interface.
Figure 9:
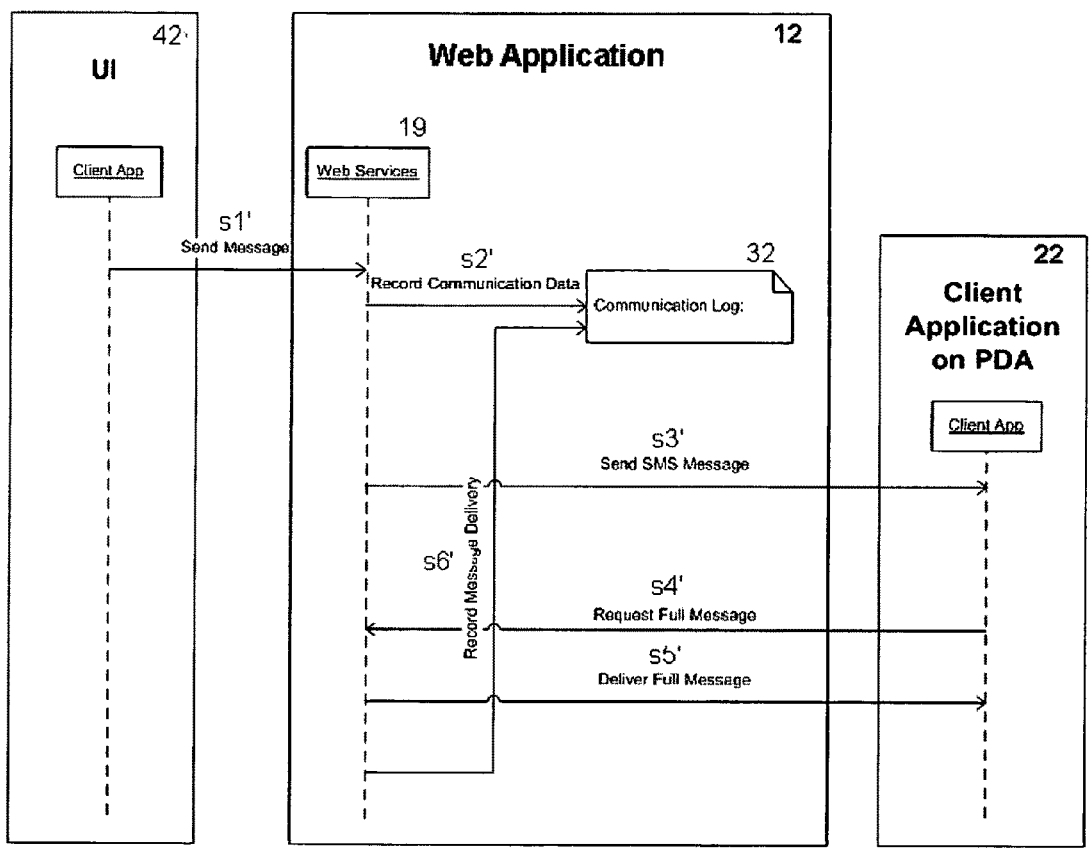
FIG. 9 is a diagrammatic illustration of the method by which a communication is transmitted by a caregiver to a sufferer using a mobile device based user interface.

The chronological steps (indicated by a parenthetical reference numeral preceded by the designation "s") that are executed by the subject system in order to enable communication between a caregiver and the sufferer, and to log the communications as described below, are depicted in FIGS. 8 and 9.

Through a Web browser depicted on the User Interface 14 of sufferer's computer 40, a caregiver navigates to Web Application 12 and selects on the appropriate Web Page one of the sufferers associated with his/her account and then navigates to the 'send message' option (not shown). The caregiver enters the message text and sends (s1) the message. The Web application records (s2) details of the message, including dates and types (i.e., text, image, voice, video), for all communications sent by each caregiver in database 18 thereby creating a communication log 32. The minimum information recorded by the Web application is as follows:
1. Caregiver's identity
2. Sufferer's identity
3. Date and time of communication
4. Type of communication (text message, picture, video)
5. Optionally, communication content Web Application 12 then sends (s3) an SMS message to the sufferer's PDA device 20, informing that there is a 'new update' ready for download. Upon receiving the 'new update' SMS message, the PDA automatically requests (s4) the full message from Web Service 19 which upon receipt of the request delivers (s5) the message to Client Application 22 for download and records (s6) the message delivery. To send pictures, video or audio-video files, the same protocol is followed by navigating to the appropriate option on the UI such as 'send picture(s)'. The caregiver uses the UI to select one or more pictures and confirms the send action. All pictures are preferably but not essentially sent with a corresponding text description of the picture to assist the sufferer in recognizing ("remembering") the people, places and/or things depicted therein. Both the picture and accompanying text are displayed on the sufferer's PDA simultaneously.

FIG. 9 illustrates the protocol used when the UI is delivered to the caregiver through a mobile device 42 like Windows Mobile based smart-phone, iPhone, or the like, rather than through a Web Based User Interface as described above. The protocols are nearly identical except the message is sent s1' from mobile device 42 to Web Services 19 of Web Application 12. The remaining steps s2' through s6' are the same.

Processing and Publishing Communication Log Data

Main .NET Web Application 16 continuously processes all logged message details of the communication logs 32 of each caregiver associated with a particular sufferer to create a Communication Mix Report that is published on each said caregiver's user interface including that of the primary caregiver. More specifically, Main .NET Web Application 16 sorts all messages transmitted to the sufferer by communication date and time starting with the most recent communication.

The Communication Mix Report displayed on each caregiver's UI may by way of example only look as follows:

| Caregiver | Sufferer | Time of Communication | Type of Communication |
| --- | --- | --- | --- |
| Jane Doe | Jane Smith | 05/14/2009 2:00 PM | Text message |
| Joe Smith | Jane Smith | 05/13/2009 10:43 AM | Picture |
| Jane Doe | Jane Smith | 05/13/2009 9:45 AM | Picture |
| John Doe | Jane Smith | 05/12/2009 5:55 PM | Video |

By continuously publishing a log of the frequency and nature of communications transmitted by caregivers to a sufferer, both primary and secondary caregivers are able to quickly glean the overall quantity and quality of communications in a single "snap-shot" view. Such information can serve as a concrete and tangible representation of the level of support being provided to the sufferer and may be of particular value to medical personnel involved in the care and treatment of the sufferer. Of equal if not greater value is that such information when published to all caregivers creates a peer pressure environment to encourage more frequent and meaningful contact with the sufferer. The term 'meaningful' as used herein means communications which are most likely to elicit sufferer memories, namely pictures, videos and the like.

In addition to the above mixed report, each individual caregiver's communication data associated with their individual Communication Log may be processed, sorted and displayed either directly on the Communication Mix Report, in order to increase peer pressure, or as a separate, drill-through report, when any user clicks on a particular caregiver's name, or the whole line, in the Communication Mix Report.

The statistics generated by the Main NET Application 16 and displayed on the Web pages of the Web Application 12 for each individual caregiver may include, for example, the following:
1. Days passed since last communication (any type)
2. Average number of days between communications
3. Days passed since last text message sent
4. Days passed since last picture sent
5. Days passed since last video sent
6. Text message over total communication ratio
7. Picture over total communication ratio
8. Video over total communication ratio Each caregiver's communication statistics may be displayed as additional columns in the Communication Mix Report, as a call out 'Details View' associated with each individual caretaker in the Communication Mix Report, or as a completely separate report. An example published report may be depicted as follows:

| Days since last comm. | Average days between comm. | Days since last text | Days since last picture | Days since last video | Text ratio | Picture ratio | Video ratio |
| --- | --- | --- | --- | --- | --- | --- | --- |
| 4 | 7 | 4 | 10 | 8 | 70% | 20% | 10% |

For each caregiver, the Main .NET Web Application calculates and assigns to each caregiver a Caregiver Rating by comparing a caregiver's communication activity, qualitatively and quantitatively, against a predetermined expected or desired level of communication as determined by the primary caregiver. A caregiver that meets the expected/desired communication goals receives five stars and so on. This rating system is used as an additional peer pressure mechanism and may be visually presented on the Communication Mix Report or individual caregiver's report substantially as follows:

Caregiver Rating: 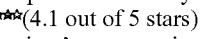(4.1 out of 5 stars)

The level of each caregiver's communication relative to that of the other caregivers associated with a particular sufferer may be calculated by the subject apparatus and published in the form of chart position. For each caregiver, a chart position is calculated as a result of a comparison of caregiver's communication quality or activity level against other caregivers supporting the same sufferer. This chart system is used as an additional peer pressure mechanism and may be presented visually as follows:

| This month | Last month | Caregiver's Name | Caregiver rating |
|---|---|---|---|
| 1 | 2. | Jane Doe | ★★★★★ |
| 2. | 1. | John Doe | ★★★★★ |
| 3. | 4. | Joe Smith | ★★★★★ |

For each group of caregivers supporting a single sufferer, a calculated Caregiver Team Rating may be calculated and assigned as a result of a comparison of a group's averaged communication quality or frequency against other groups of caregivers supporting other sufferers. Unlike the individual Caregiver Rating, the group's expected/desired communication activity/quality level is not pre-determined, but rather calculated dynamically by using a curved rating. The group of caregivers supporting a single sufferer that has the highest averaged individual Caregiver Rating receives five stars. The group of caregivers supporting a single sufferer that has the lowest averaged individual Caregiver Rating receives one star, and all other groups of caregivers are rated in comparison to the aforementioned two groups. This rating system is used as an additional peer pressure mechanism on each group of caregivers and is published in different places within the UI in a form similar to the following:

Group Rating: ★★★★★(4.1 out of 5 stars)

Another important feature of the subject system is that the Web application 12 can also be programmed to send periodic electronic reminders to all caregivers who opt-in to the service prompting them to send a communication to the sufferer. The period of caregiver's inactivity that will trigger the electronic reminder to be sent or displayed is pre-set by the primary caregiver or other administrator of the Web application, and is defined as the number of days since the last communication. After the specified time period since the last communication by each caregiver expires, the Web application will automatically use at least one of the four methods described below to alert a specific caregiver that transmission of a communication to the sufferer is required.

Figure 10:
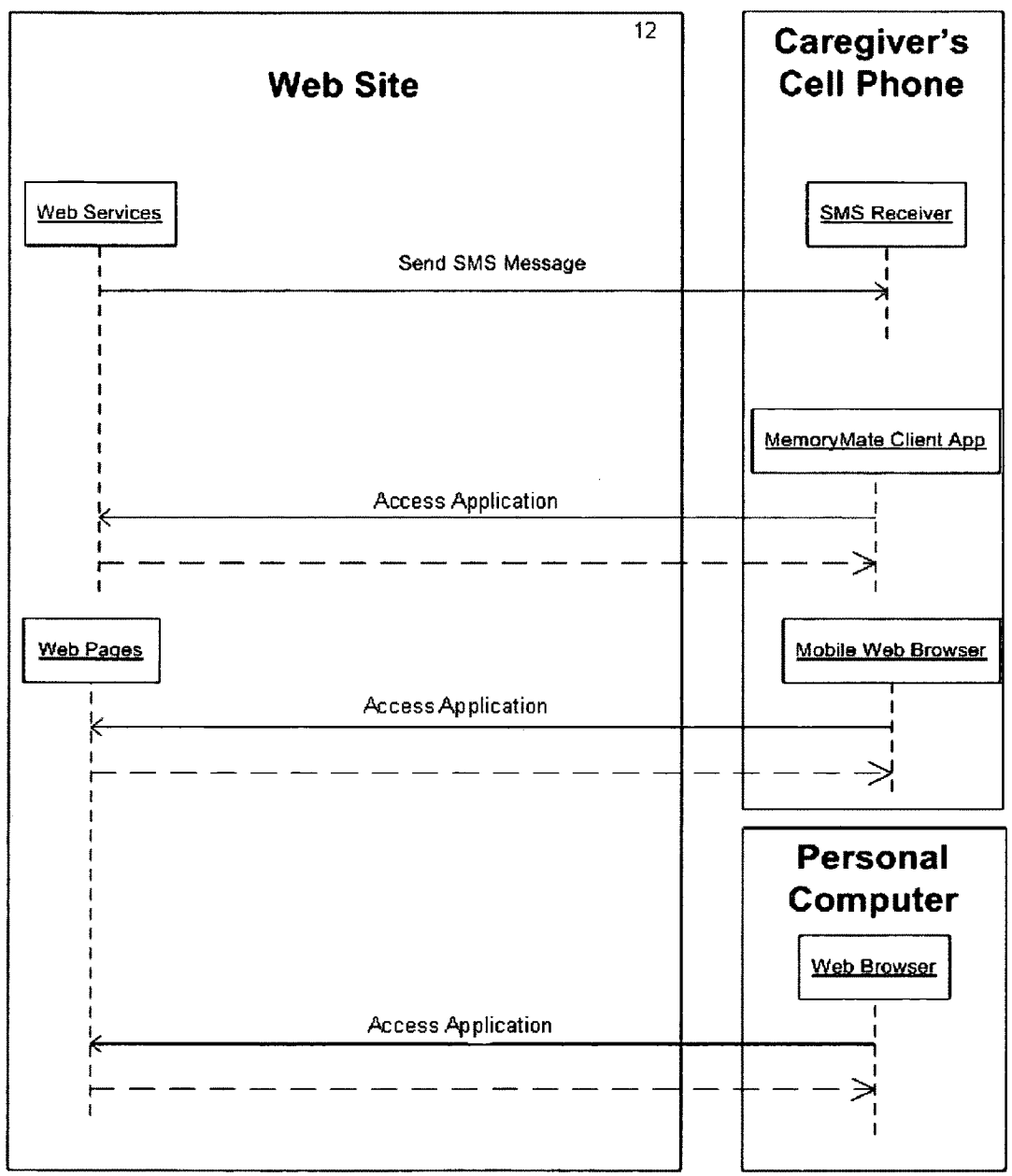
FIG. 10 is a diagrammatic illustration of the manner in which the subject system prompts a caregiver, via SMS, to transmit a communication to a sufferer.

Referring to FIG. 10, the Web application sends an SMS message to a caregiver. The message reminds the caregiver that he or she was inactive for a period of time and instructs the caregiver to send a communication to the sufferer. The message also contains a direct link to either the Web based UI provided by the Web application, or to the UI on the mobile device that received the SMS message, which caregiver can use to login to Caregiver's UI in order to send a communication. The caregiver can also use his or her personal computer to access the UI.

Figure 11:
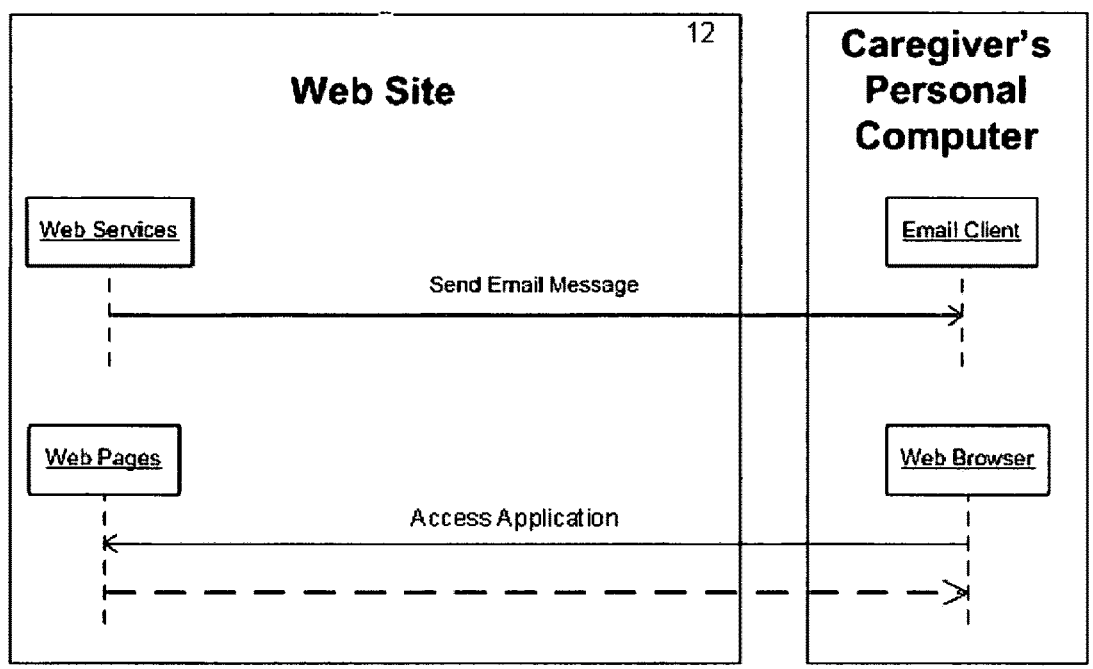
FIG. 11 is a diagrammatic illustration of the manner in which the subject system prompts a caregiver, via email, to transmit a communication to a sufferer.

Referring to FIG. 11, the Web application sends an email message to a caregiver. The message reminds the caregiver that he or she was inactive for a period of time and instructs the caregiver to send a communication to the sufferer. The message may also contain a direct link to either the Web based UI provided by the Web application, or to the UI on the mobile device that received the email message, which the caregiver can use to login to his/her UI in order to send a communication.

Figure 12:
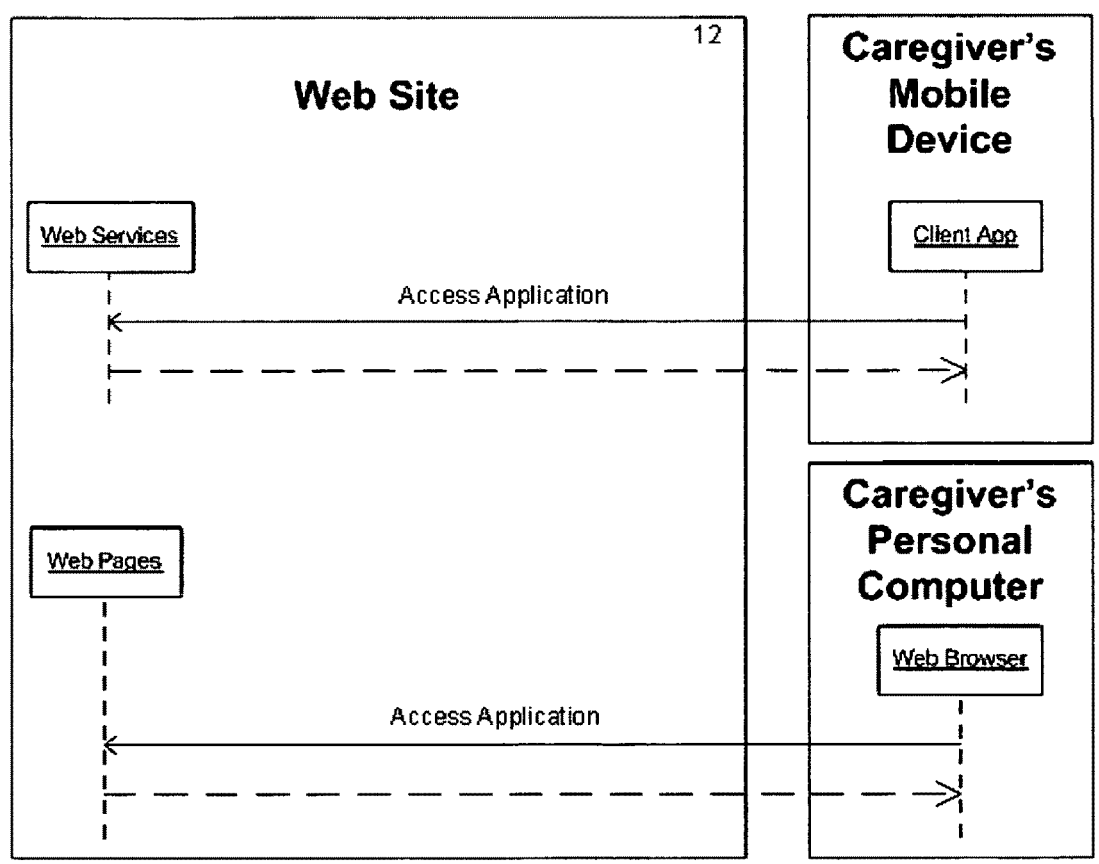
FIG. 12 is a diagrammatic illustration of the manner in which the subject system prompts a caregiver, via the caregiver's Web mobile device or personal computer, to transmit a communication to a sufferer.

Referring to FIG. 12, the caregiver's UI (whether Web based or on a mobile device) displays and/or sounds an alert reminding the caregiver that he or she was inactive for a period of time and prompts the caregiver to send a communication to the sufferer. The alert also contains a direct link to either the Web based UI provided by the Web application, or to the UI on the mobile device that displayed an alert, which caregiver can use to login to Caregiver's UI in order to send a communication.

Figure 13:
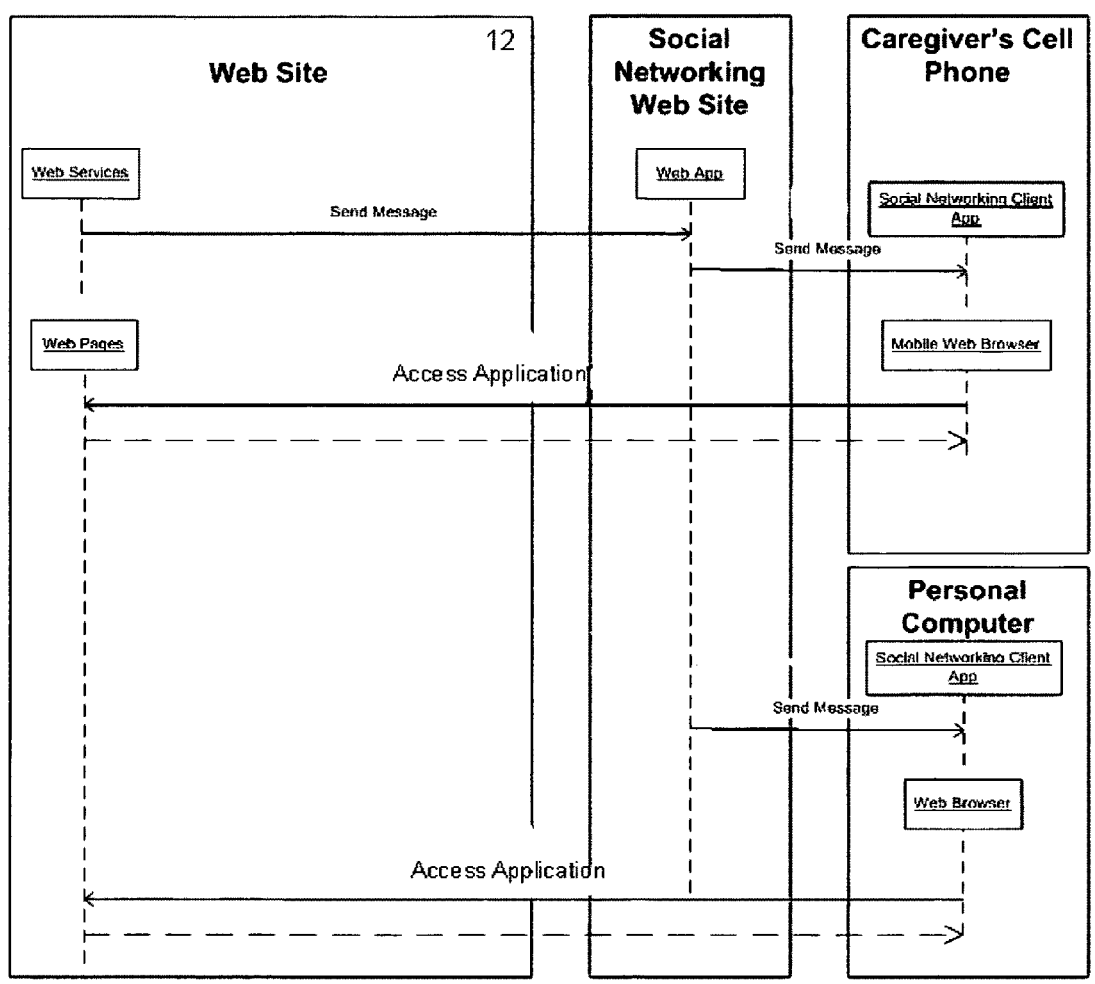
FIG. 13 is a diagrammatic illustration of the manner in which the subject system prompts a caregiver, via a social networking platform, to transmit a communication to a sufferer.

Referring to FIG. 13, the Web application sends a communication to a caregiver through any publicly available Social Networking/Messaging Web Site/Service like Twitter, Facebook, MySpace, etc. A custom widget/gadget or similar form of plug-in may be developed for a specific Web site/service that will integrate seamlessly with the Web site's/service's User-interface, receive communication from the Web application and display alerts. The technical implementation of communication between the Web application and the widget/gadget/plug-in will depend largely on an individual Web site/service targeted.

While exemplary systems and methods embodying the present invention are shown by way of example, it will be understood, of course, that the invention is not limited to these embodiments. Modifications may be made by those skilled in the art, particularly in light of the foregoing teachings. For example, each of the elements of the aforementioned embodiments may be utilized alone or in combination with elements of the other embodiments.

What is claimed as being new, useful and desired to be protected by Letters Patent of the United States is as follows:

1. A system for encouraging frequent and purposeful electronic communications from caregivers to a person with impaired memory, the system comprising:
   a. a computing device operated by a person with impaired memory; said first computing device having means for receiving communications from other devices;
   b. at least one caregiver computing device having a Web browser and operated by at least one caregiver of the person;
   c. a Web application running on a Web server, said Web application being operably connected to said computing device and to said at least one caregiver communication device via a communications infrastructure; said Web application comprising:
      i. means for receiving communications data from said at least one caregiver computing device and for sending said communications data to the person with impaired memory;
      ii. means for recording the time and type of said communications data; said type of said communications data being at least one type selected from the group consisting of text, audio, picture and video data intended to invoke memories of the person with impaired memory;
      iii. means for processing said communications data and for publishing a report of processed communications data on a Web page accessible by said at least one caregiver, said report comprising communication statistics useful in assessing the frequency and quality of communications sent by each at least one caregiver to the person with impaired memory.

2. The system of claim 1 wherein said Web application further includes means for sending alerts to said at least one caregiver, said alerts prompting said at least one caregiver to send the person with impaired memory a communication, said alerts being sent when a predefined period of time has elapsed since said at least one caregiver's last communication to the person with impaired memory.

3. The system of claim 1 wherein said report includes at least one of the following communication data for each at least one caregiver:
   a. Days passed since last communication of any type;
   b. Average number of days between communications;
   c. Days passed since last text message sent;
   d. Days passed since last picture sent;
   e. Days passed since last video sent;
   f. Text message over total communication ratio;
   g. Picture over total communication ratio;
   h. Video over total communication ratio.

4. The system of claim 3 wherein said Web application further includes means for rating each of said at least one caregiver's communication activity based on a comparison of said communication data with predetermined desired levels of communication.

5. The system of claim 3 wherein said Web application further includes means for ranking each of said at least one caregiver by their level of communication activity relative to one another.

6. The system of claim 5 wherein said ranking is based on at least one factor selected from the group consisting of:
   a. frequency of communication with the person with impaired memory; and
   b. the level of utilization of each of said type of communication data.

* * * * *